US00PP09370P

United States Patent [19]

VandenBerg

[11] Patent Number: Plant 9,370

[45] Date of Patent: Nov. 14, 1995

[54] CHRYSANTHEMUM PLANT NAMED 'AMI'

[75] Inventor: Cornelis P. VandenBerg, Salinas, Calif.

[73] Assignee: Yoder Brothers, Inc., Barberton, Ohio

[21] Appl. No.: 331,864

[22] Filed: Nov. 1, 1994

[51] Int. Cl.[6] ..... A01H 5/00

[52] U.S. Cl. ..... Plt./82.2

[58] Field of Search ..... Plt./82.2

[56] References Cited

U.S. PATENT DOCUMENTS

P.P. 7,759 12/1991 VandenBerg ..... Plt./82.2
P.P. 8,610 2/1994 VandenBerg ..... Plt./82.2

*Primary Examiner*—Howard J. Locker
*Attorney, Agent, or Firm*—Foley & Lardner

[57] ABSTRACT

A Chrysanthemum plant named Ami particularly characterized by its flat capitulum form; daisy capitulum type; yellow ray floret color, diameter across face of capitulum of 29 to 32 mm when fully opened, when grown as a pinched spray pot mum; very floriferous with excellent display of many small flowers; photoperiodic flowering response to short days of 47 to 56 days; plant height, with 20 to 26 long days after sticking unrooted cuttings prior to start of short days and with 1 application of 2500 ppm B-9 SP, ranging from 18 to 24 cm when grown as a pinched pot mum with 4 cuttings in a 15 cm pot; and spreading and prolific branching pattern, each plant having 5 to 8 laterals after pinch.

3 Drawing Sheets

The present invention comprises a new and distinct cultivar of Chrysanthemum, botanically known as *Dendranthema grandiflora,* and referred to by the cultivar name Ami.

Ami, identified as 5031 (89-256009), was originated from a cross made by Cornelis P. VandenBerg in a controlled breeding program in Salinas, Calif., in 1989.

The female parent of Ami was the cultivar identified as Blondelle, disclosed in U.S. Plant Pat. No. 7,759, and described as a daisy spray pot mum with flat capitulum form; yellow ray floret color; diameter of capitulum of 32 to 38 mm; flowering response to short days of 48 to 54 days; plant height of 20 to 28 cm when grown as a pinched spray pot mum with 4 cuttings in a 15 cm pot and with 14 to 16 long days after sticking unrooted cuttings prior to start of short days, and 1 to 2 applications of 2500 ppm B-9 SP; and a spreading and prolific branching pattern, with 5 to 7 branches developing per plant after pinch.

The male parent of Ami was an unnamed seedling, identified as 86-664003, and described as a flat daisy spray pot mum with yellow ray floret color; diameter of capitulum of 41 to 51 mm; flowering response to short days of 48 to 54 days under normal conditions; plant height of 23 to 28 cm with 15 to 16 long days after sticking unrooted cuttings prior to start of short days, and 1 to 2 applications of 2500 ppm B-9 SP; and a spreading and prolific branching pattern, with 5 to 7 breaks developing per plant after pinch. The male parent was discarded from the program in August 1989.

Ami was discovered and selected as one flowering plant within the progeny of the stated cross by Cornelis P. VandenBerg in April 1990, in a controlled environment in Salinas, Calif.

The first act of asexual reproduction of Ami was accomplished when vegetative cuttings were taken from the initial selection in June 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Ami are firmly fixed and are retained through successive generations of asexual reproduction.

Ami has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Ami, which, in combination, distinguish this Chrysanthemum as a new and distinct cultivar:

1. Flat capitulum form.
2. Daisy capitulum type.
3. Yellow ray floret color.
4. Diameter across face of capitulum of 29 to 32 mm when fully opened, when grown as a pinched spray pot mum.
5. Very floriferous with excellent display of many small flowers.
6. Photoperiodic flowering response to short days of 47 to 56 days.
7. Plant height, with 20 to 26 long days after sticking unrooted cuttings prior to start of short days and with 1 application of 2500 ppm B-9 SP, ranges from 18 to 24 cm when grown as a pinched pot mum with 4 cuttings in a 15 cm pot.
8. Small dark green foliage.
9. Branching pattern is spreading and prolific, each plant having 5 to 8 laterals after pinch.

The accompanying photographic drawings show typical inflorescence and leaf characteristics of Ami, with the colors being as nearly true as possible with illustrations of this type.

Sheet 1 is a color photograph of Ami grown as a pinched spray pot mum with 4 cuttings in a 15 cm pot.

Sheet 2 is a black and white photograph of three views of the inflorescence of Ami.

Sheet 3 is a black and white photograph showing the upper and under sides of the leaves of Ami at 3 stages of development (mature, intermediate and immature). In sheets 2 and 3 a measuring tape in centimeters has been added.

Of the commercial cultivars known to the inventor, the most similar in comparison to Ami is the cultivar identified as Alouette, disclosed in U.S. Plant Pat. No. 7,468. Reference is made to attached Chart A, which compares certain characteristics of Ami to the same characteristics of Alouette.

Similar traits are capitulum form and type, flowering response to short days, and branching pattern, with Ami developing on less lateral after pinch in some flowering trials than Alouette. The ray floret color of both Ami and Alouette is described as yellow. However, Ami has a lighter upper surface yellow ray floret color (5A) than Alouette (9A). In addition, Alouette has a red-bronze underside of the ray florets, while the ray floret color of Ami is clear yellow. Ami also has a smaller diameter of capitulum and a shorter plant height when compared with Alouette.

In the following description color references are made to The Royal Horticultural Society Colour Chart. The color values were determined on plant material grown as a pinched spray pot mum in Salinas, Calif. on Aug. 5, 1994.

Classification:

*Botanical.*—*Dendranthema grandiflora* cv. Ami.

*Commercial.*—Daisy spray pot mum.

INFLORESCENCE

A. Capitulum:

*Form.*—Flat.

*Type.*—Daisy.

*Diameter across face.*—29 to 32 mm when fully opened.

B. Corolla of ray florets:

*Color (general tonality from a distance of three meters).*—Yellow.

*Color (upper surface).*—5A.

*Color (under surface).*—6A.

*Shape.*—Straight, flat, rounded apex.

C. Corolla of disc florets:

*Color (mature).*—14B.

*Color (immature).*—14B, overlaid with 144B.

D. Reproductive organs:

*Androecium.*—Present on disc florets only; scant pollen.

*Gynoecium.*—Present on both ray and disc florets.

PLANT

A. General appearance:

*Height.*—18 to 24 cm when grown as a pinched pot mum in a 15 cm pot with 20 to 26 long days after direct sticking unrooted cuttings and 1 application of 2500 ppm B-9 SP.

*Branching pattern.*—Spreading and prolific, with 5 to 8 laterals after pinch.

B. Foliage:

*Color (upper surface).*—147A.

*Color (under surface).*—147B.

*Shape.*—See photograph.

CHART A

| CHARACTERISTICS | AMI | ALOUETTE |
|---|---|---|
| Ray floret color | Yellow | Yellow with red-bronze underside |
| Capitulum form and type | Flat daisy | Flat daisy |
| Diameter across face of capitulum | 29 to 32 mm | 38 to 45 mm |
| Flowering response | 47 to 56 days | 46 to 56 days |
| Plant height with | | |
| 20 to 26 long days | 18 to 24 cm | |
| 16 to 23 long days | | 20 to 25 cm |
| Branching pattern | Spreading 5 to 8 laterals | Spreading 6 to 8 laterals |

COMPARISONS MADE OF PLANTS GROWN AS PINCHED SPRAY POT MUMS IN SALINAS, CALIFORNIA

I claim:

1. A new and distinct Chrysanthemum plant named Ami, as described and illustrated.

* * * * *

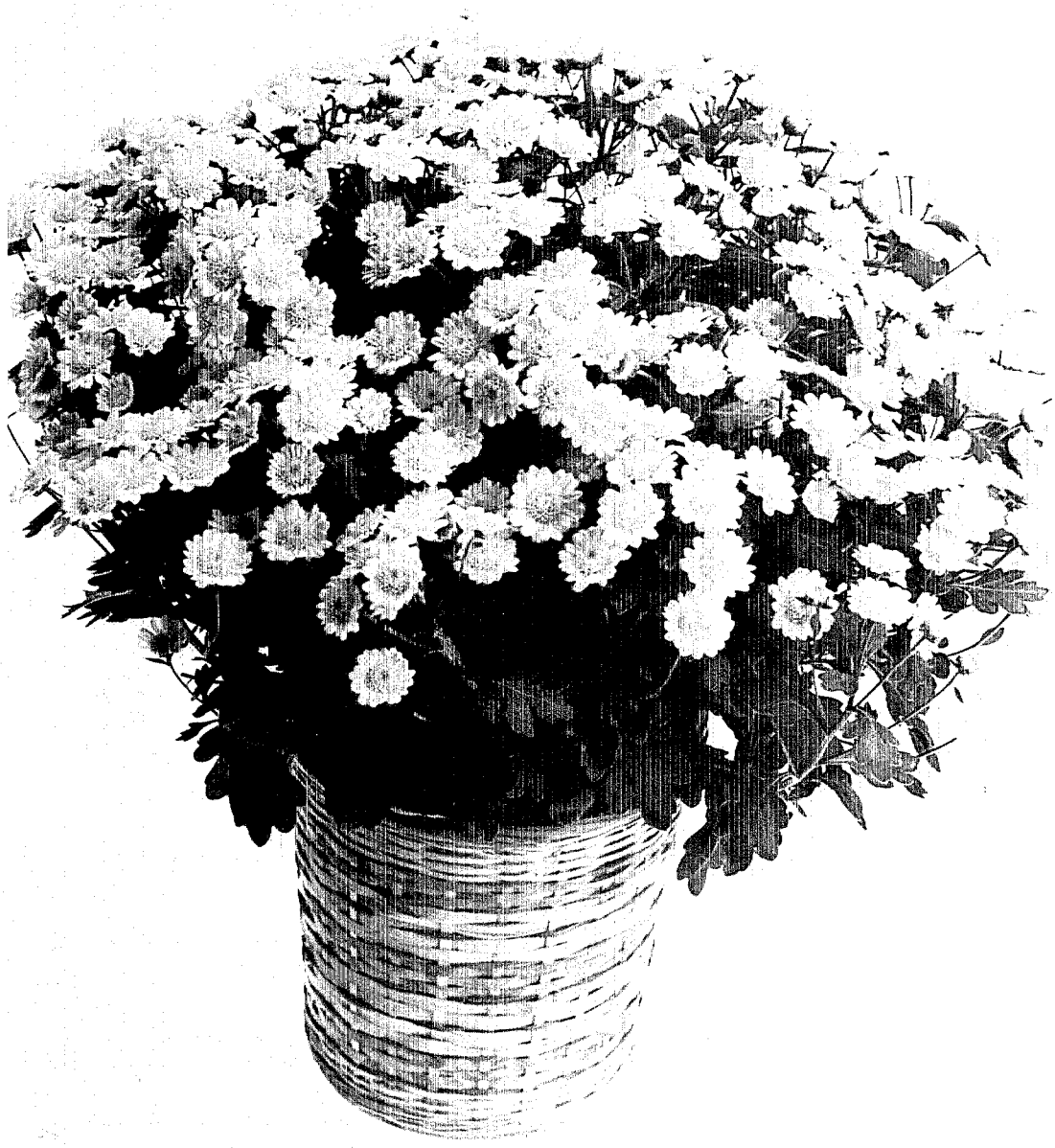

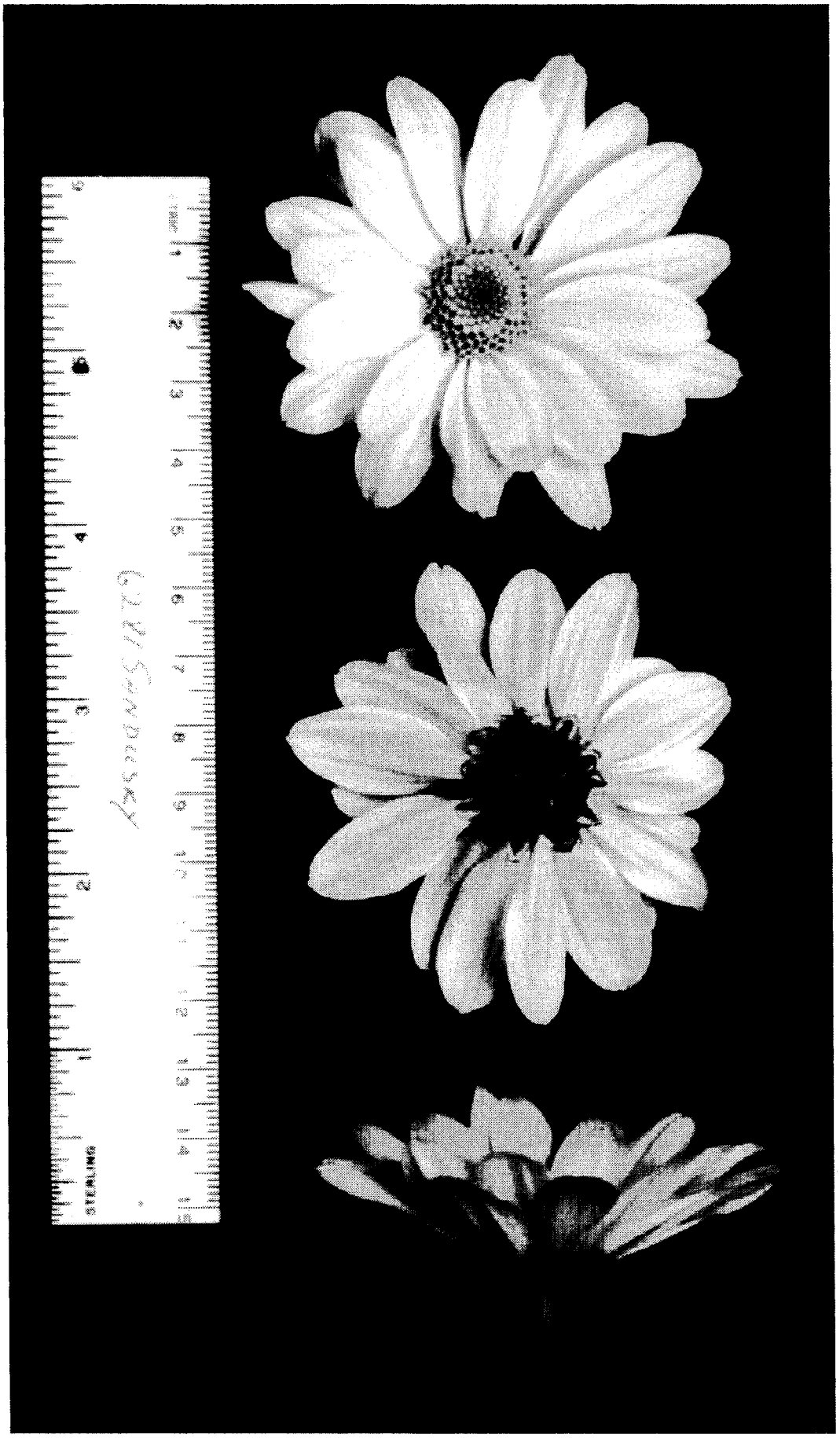
STERLING
Gerbera

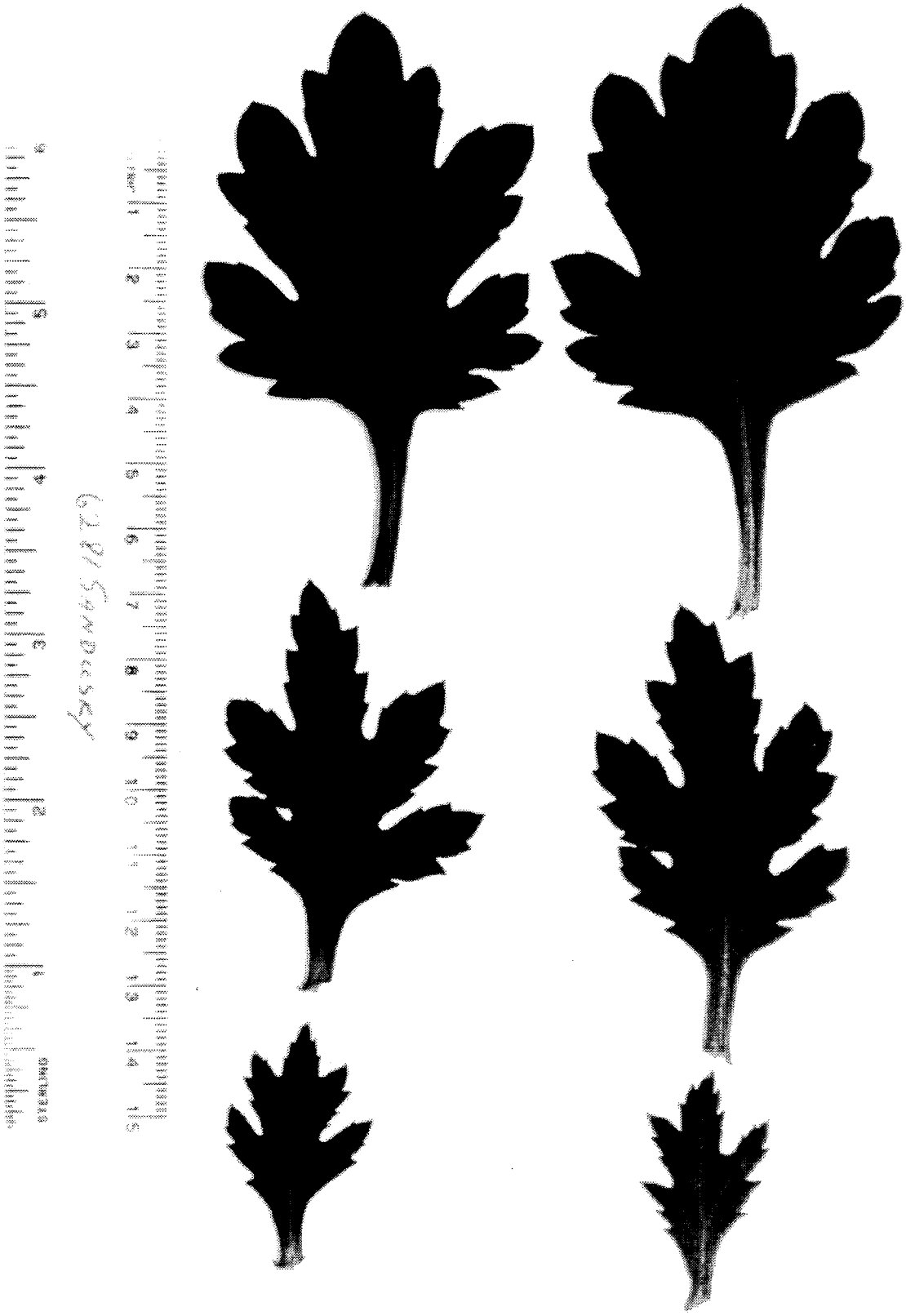
Calif Sunbrassy